United States Patent
Ziegenfuss et al.

(10) Patent No.: US 10,993,978 B1
(45) Date of Patent: *May 4, 2021

(54) COMPOSITIONS AND METHODS FOR INCREASE IN MUSCLE VOLUME

(71) Applicant: KLZ Holdings, LLC, Manasquan, NJ (US)

(72) Inventors: Tim N. Ziegenfuss, Chardon, OH (US); Hector L. Lopez, Cream Ridge, NJ (US); Bruce W. Kneller, Howell, NJ (US)

(73) Assignee: KLZ HOLDINGS, LLC, Manasquan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/143,106

(22) Filed: Jan. 6, 2021

Related U.S. Application Data

(62) Division of application No. 16/868,359, filed on May 6, 2020, now Pat. No. 10,925,911.

(51) Int. Cl.
*A61K 36/00* (2006.01)
*A61K 36/185* (2006.01)
*A61P 21/06* (2006.01)
*A61K 9/00* (2006.01)
*A61K 31/047* (2006.01)

(52) U.S. Cl.
CPC .......... *A61K 36/185* (2013.01); *A61K 9/0053* (2013.01); *A61K 31/047* (2013.01); *A61P 21/06* (2018.01)

(58) Field of Classification Search
None
See application file for complete search history.

(56) References Cited

U.S. PATENT DOCUMENTS

2006/0280698 A1* 12/2006 Gupta .................. A61K 8/9789
424/50

* cited by examiner

*Primary Examiner* — Qiuwen Mi
(74) *Attorney, Agent, or Firm* — Umberg Zipser LLP

(57) ABSTRACT

Compositions and methods include a synergistically effective combination of glycerol and *Phyllanthus emblica* extract for increasing muscle volume in response to an exercise stimulus of the corresponding muscle or muscle region.

12 Claims, No Drawings

COMPOSITIONS AND METHODS FOR INCREASE IN MUSCLE VOLUME

This application is a divisional application of allowed U.S. application Ser. No. 16/868,359, which was filed May 6, 2020, incorporated by reference herein.

FIELD OF THE INVENTION

The field of the invention relates to compositions and methods for increasing muscle volume, increasing lean body mass, and/or increasing physical performance, by administering an effective combination of glycerol and *Phyllanthus emblica* to the subject.

BACKGROUND

The following description includes information that may be useful in understanding the present invention. It is not an admission that any of the information provided herein is prior art or relevant to the presently claimed invention, or that any publication specifically or implicitly referenced is prior art.

A desire for enhanced physical performance, endurance, as well as increased muscle volume and lean body mass is desired by both professional and amateur athletes as well as even more sedentary persons. For professional athletes, the pressure to perform corresponds with career success, and many non-professional persons who want to be athletic or at least have an athletic look, also desire a high level of performance and muscle.

Regardless of the athletic level of a person, a demand for performance enhancing drugs has remained among both professionals and amateurs alike despite many of these drugs being banned, illegal, and having unhealthy side effects. Thus, there is a need for safe and legal performance enhancing options, such as natural products or nutraceuticals for improving performance, endurance, and/or muscle size for persons at any level of physical activity or overall body fitness.

SUMMARY OF THE INVENTION

The inventive subject matter provides a composition in the form of a synergistic combination of glycerol and *Phyllanthus emblica* extract for increasing muscle volume, increasing lean body mass, and/or increasing physical performance in a subject.

More specifically, a composition as disclosed herein includes an effective dosage of the synergistic combination in which the active ingredients imparting synergy are glycerol at between 0.1 to 25 grams and *Phyllanthus emblica* extract at between about 0.03 to 1.0 gram.

In some embodiments the synergistic active ingredients of the composition are present in a weight ratio of *Phyllanthus emblica* to glycerol of between 1:1 to 1:25. Preferably, the active ingredients are present in a weight ratio of *Phyllanthus emblica* to glycerol of between 1:3 to 1:10.

Typically, the *Phyllanthus emblica* extract in the composition includes not less than 5% of low molecular weight hydrolysable tannins.

In additional embodiments, in addition to the synergistic active ingredients, the composition also includes one or more additives selected from a medium chain triglyceride, a short chain triglyceride, a short chain fatty acid, a botanical flavonoid, a botanical phenylpropanoid, an amino acid, an amino acid salt, an amino acid ester, an amino acid chelate, a nitrate salt, a vasoactive peptide, a protein isolate, and/or a protein concentrate.

In exemplary embodiment, the one or more additives are selected from piceatannol, epicatechin, flavan-3-ols, resveratrol, pterostilbene, quercetin, theaflavin, kaempferol, hesperidin, caffeine, theacrine, methylliberine, dextrose, sucrose, maltodextrin, ribose, amylose, isomaltulose, amylopectin, rice oligodextrin, cluster dextrins, whey protein concentrate, whey protein isolate, egg protein, beef protein, potato protein, calcium caseinate, rice protein concentrate, rice protein isolate, pea protein, hemp protein, and/or combinations thereof.

In other additional embodiments, the composition of an effective dosage is a daily dose which may be formulated as powder to be mixed in a liquid or in a solid dosage form to be formed as one or more tablets, one or more caplets, one or more capsules, one or more lozenges, one or more nutritional bars, one or more food bars, one or more candy bars, or a ready-to-mix/ready-to-drink formulation.

The contemplated composition may also be a dietary supplement having an effective dosage of active ingredients, in which the only active ingredients are glycerol at between about 0.1 to 25 grams and *Phyllanthus emblica* extract at between about 0.03 to 1.0 gram.

In specific embodiments, the active ingredients of the dietary supplement are present in a weight ratio of *Phyllanthus emblica* to glycerol of between 1:1 to 1:25.

In other specific embodiments, the *Phyllanthus emblica* extract in the dietary supplement includes not less than 5% of low molecular weight hydrolysable tannins.

In further embodiments, the dietary supplement having a synergistic combination of glycerol and *Phyllanthus emblica* extract also includes one or more additives. In some embodiments, the additive is selected from one or more of a medium chain triglyceride, a short chain triglyceride, a short chain fatty acid, a botanical flavonoid, a botanical phenylpropanoid, an amino acid, an amino acid salt, an amino acid ester, an amino acid chelate, a nitrate salt, a vasoactive peptide, a protein isolate, and/or a protein concentrate.

In exemplary embodiments, the additive is one or more selected from piceatannol, epicatechin, flavan-3-ols, resveratrol, pterostilbene, quercetin, theaflavin, kaempferol, hesperidin, caffeine, theacrine, methylliberine, dextrose, sucrose, maltodextrin, ribose, amylose, isomaltulose, amylopectin, rice oligodextrin, cluster dextrins, whey protein concentrate, whey protein isolate, egg protein, beef protein, potato protein, calcium caseinate, rice protein concentrate, rice protein isolate, pea protein, hemp protein, and/or combinations thereof.

The contemplated subject matter also includes a method of increasing muscle volume or increasing lean body mass in a muscle or muscle region in a subject. The inventive method includes administering glycerol to the subject, administering *Phyllanthus emblica* extract to the subject, and exercising the muscle or the muscle region of the subject, wherein the glycerol is administered in a daily dosage at between 0.10 to 25 grams and the *Phyllanthus emblica* extract is administered in a daily dosage at between about 0.03 to 1.0 gram.

In typical embodiments, the disclosed inventive method for increasing muscle volume or increasing lean body mass includes administering the glycerol and the *Phyllanthus emblica* extract either concurrently or sequentially in any order.

In some embodiments, the disclosed inventive method for increasing muscle volume or increasing lean body mass includes administering the *Phyllanthus emblica* extract and the glycerol in a weight ratio of between about 1:1 to 1:25.

In more specific embodiments, the disclosed inventive method for increasing muscle volume or increasing lean body mass includes administering the glycerol at between 9.25 to 11.30 mg per kilogram (mg/kg) weight of the subject and administering the *Phyllanthus emblica* extract at between 1.58 to 1.93 mg/kg weight of the subject.

The contemplated method as disclosed herein may also include administering the glycerol and the *Phyllanthus emblica* extract concurrently in a formulation as a powder to be mixed in a liquid or in a solid dosage form to be formed as one or more tablets, one or more caplets, one or more capsules, one or more lozenges, one or more nutritional bars, one or more food bars, one or more candy bars or a ready-to-mix/ready-to-drink formulation.

The contemplated method for increasing muscle volume or increasing lean body mass as disclosed herein may also include a period of at least 10 minutes between administering the disclosed synergistic composition (made of at least the glycerol and the *Phyllanthus emblica* extract) and beginning the exercise session. Furthermore, the muscle or the muscle region may be measured prior to the administering of the synergistic composition and the method may also include measuring the muscle or the muscle region after the exercising. In exemplary embodiments, measuring the girth of the muscle or the muscle region and the increase in lean body mass includes using Dual-energy X-ray absorptiometry (DEXA).

In additional or alternative embodiments, the inventive subject matter includes a method for transiently or acutely increasing muscle volume or lean body mass in a subject with administering glycerol to the subject, administering *Phyllanthus emblica* extract to the subject, and exercising the muscle or the muscle region of the subject.

Various objects, features, aspects and advantages of the inventive subject matter will become more apparent from the following detailed description.

DETAILED DESCRIPTION

The inventors have contemplated advantageous compositions and methods for increasing muscle volume, increasing lean body mass, and/or increasing physical performance in a subject. The inventive subject matter includes a synergistic combination of glycerol and *Phyllanthus emblica* extract as well as methods for increasing muscle volume and mass in response to an exercise stimulus by administering the synergistic combination of glycerol and *Phyllanthus emblica* extract to a subject prior to exercising the muscle.

The effective combination of glycerol and *Phyllanthus emblica* extract provides a synergistic effect by conferring an unexpected increase in muscle volume and lean body mass in a subject ingesting this combination prior to muscle use. That is, the increase in muscle volume and lean body mass and/or increase in physical performance is not conferred at the same level when the subject ingests (e.g., by oral administration) a composition of glycerol alone or *Phyllanthus emblica* extract alone, and the synergistic increase is more than an additive result.

Accordingly, as used herein, "consisting essentially of" refers to those elements (e.g., components or ingredients) required for a given embodiment. The term "consisting essentially of" permits the presence of additional elements that do not materially affect the basic and novel or functional characteristic(s) of that embodiment of the invention. More specifically, "consisting essentially of" refers to the synergistic active ingredients (e.g., glycerol and *Phyllanthus emblica* extract) capable of effecting an increase in muscle volume and/or body mass. Additional additives or excipients which may add additional health benefits may be combined with a composition consisting essentially of the synergistic active ingredients.

The *Phyllanthus emblica* is a medicinal plant commonly referred to as Indian gooseberry or amla and is used in the ayurvedic medicine. The contemplated effective composition includes an extract of *Phyllanthus emblica*. For effective results, any extract of *Phyllanthus emblica* may be combined with glycerol as disclosed herein. Preferably, the *Phyllanthus emblica* extract includes not less than 5% of low molecular weight hydrolysable tannins. In some exemplary embodiments the *Phyllanthus emblica* extract includes not less than 5%, 10%, 15%, 20%, 25%, 30%, 35%, 40%, 45%, 50%, or 60% of low molecular weight hydrolysable tannins. In more preferred embodiments, the low molecular weight hydrolysable tannins include emblicanin-A, emblicanin-B, punigluconin and/or pedunculagin.

Glycerol (IUPAC ID: propane=1,2,3-triol, CAS NO. 56-81-5) is considered generally recognized as safe (GRAS) by the Food and Drug Administration (FDA) for food packaging and as a multiple purpose food substance. See, 21 CFR 182.90, 21 CFR 182.132. Accordingly, any suitable form of glycerol may be combined with the *Phyllanthus emblica* extract. Due to the viscous nature of glycerol, it is may be more easily administered as part of a formulation of a dietary supplement and/or in powder form. For example, as a powder, glycerol may be formulated as a shelf stable product when agglomerated to a walling agent or suitable carrier, including but not limited to silica, silicon dioxide, calcium silicate, Acacia gums and/or resins. Preferably, glycerol powder blends are made of at least 10% glycerol. In exemplary embodiments, glycerol powder blends are made of at least 10%, 15%, 20%, 25%, 30%, 35%, 40%, 45%, 50%, 55%, 60%, or 65% glycerol. More preferably, glycerol powder blends are made of at least 20% glycerol. Most preferably, glycerol powder blends are made of at least 65% glycerol. An example of a stable glycerol powder agglomerated with silica is HydroMax® manufactured by Glanbia Nutritionals.

The contemplated compositions and methods disclosed herein are for administration to a subject desiring an increase in muscle volume and lean body mass and/or an increase in physical performance. The subject herein includes a male or female mammal and is preferably a male or female human.

Specifically, the contemplated composition is an effective combination of glycerol and *Phyllanthus emblica* extract in a supplement composition and may be in combination with other ingredients such as additives, fillers, and/or excipients so long as the effective, synergistic active ingredients of glycerol and *Phyllanthus emblica* extract are both provided. In some embodiments, the supplement composition includes *Phyllanthus emblica* extract and the glycerol in a weight ratio of between about 1:1 to 1:25.

Considered from a different perspective, the contemplated composition is an effective combination of glycerol and *Phyllanthus emblica* extract in a supplement composition in which the glycerol and *Phyllanthus emblica* extract make up at least 5% by weight of the total weight of all ingredients in a supplement composition. More specifically, the effective combination of glycerol and *Phyllanthus emblica* extract may make up at least 5%, 10%, 15%, 20%, 25%, 30%, 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% by weight of the total weight of all ingredients in a supplement composition.

As used herein, "effective dosage" refers to compositions and formulations of at least glycerol and *Phyllanthus emblica* extract in the disclosed amounts and/or ratios for effecting an increase in muscle volume, increase in lean body mass, and/or an increase in physical performance in a subject. The effective amounts of compositions may vary according to factors such as age, sex, training status, body composition, and body weight of the subject. Dosage regime may be adjusted to provide optimum response. Several divided dosages may be administered daily, or the dosage may be proportionally reduced as indicated by the exigencies of a subject's situation. As will be readily appreciated, a composition in accordance with aspects and embodiments herein is also referred to as an effective dosage and may be administered in a single serving or multiple servings spaced throughout the day. As will readily be understood by those skilled in the art, servings need not be limited to daily administrations and may be on every second day or third day or other convenient effective basis. The administration on a single day may be in single servings or multiple servings spaced throughout the day depending on the exigencies of the situation.

Notably, the effective dosage of glycerol and *Phyllanthus emblica* extract includes glycerol at between about 0.1 to 25 grams and *Phyllanthus emblica* extract at between about 0.03 to 1.0 gram. Preferably, the effective dosage of glycerol and *Phyllanthus emblica* extract includes a weight ratio of *Phyllanthus emblica* to glycerol of between 1:1 to 1:25. More preferably, the active ingredients are present in a weight ratio of *Phyllanthus emblica* to glycerol of between 1:1 to 1:20, 1:1 to 1:15, 1:1 to 1:10, 1:2 to 1:20, 1:2 to 1:15, 1:3 to 1:15, 1:3 to 1:14, 1:3 to 1:13, 1:3 to 1:12, 1:3 to 1:11, 1:3 to 1:10, 1:3 to 1:9, 1:3 to 1:8, 1:3 to 1:7, 1:3 to 1:6, 1:4 to 1:6, 1:5 to 1:6, or 1:5, 1:5.25, 1:5.5, 1:5.7, 1:5.8, 1:5.9, or 1:6. Most preferably, the active ingredients are present in a weight ratio of *Phyllanthus emblica* to glycerol of between 1:3 to 1:6, including 1:4 to 1:6, 1:5 to 1:6, or 1:5, 1:5.25, 1:5.5, 1:5.7, 1:5.8, 1:5.9, or 1:6.

Additionally, or alternatively, an effective dosage includes a composition or multiple compositions providing of between about 0.10 to 25.00 grams glycerol per day to a subject. Preferably, the effective dosage composition(s) provides of between about 0.50 to 20.00 grams glycerol per day, about 1.00 to 10.00 grams glycerol per day, or about 1.50 to 5.00 grams glycerol per day to a subject. The effective dosage of glycerol is administered sequentially in any order or concurrently with (e.g. in the same single composition or in two separate compositions administered simultaneously) of between about 30.00 to 1000.00 milligrams per day *Phyllanthus emblica* extract. Preferably, the effective dosage composition(s) provides of between about 50.00 to 750.00 milligrams *Phyllanthus emblica* extract per day, about 100.00 to 600.00 milligrams *Phyllanthus emblica* extract per day, or about 125.00 to 500.00 milligrams *Phyllanthus emblica* extract per day to a subject.

Additionally or alternatively, an effective dosage includes a composition or multiple compositions providing of between about 9.25 to 11.30 mg per kg weight of the subject per day (mg/kg/day) of glycerol which is provided in either sequential order or concurrently with (e.g. in the same single composition or in two separate compositions administered simultaneously) about 1.58 to 1.93 mg/kg/day of *Phyllanthus emblica* extract.

Additionally or alternatively, an effective dosage includes a composition or multiple compositions providing of between about 1708-1965 mg/square meter (m2) of a subject's body surface area per day of glycerol which is provided in either sequential order with or concurrently with (e.g. in the same single composition) about 291 to 336 mg/m2 of a subject's body surface area per day of *Phyllanthus emblica* extract.

Advantageously, the contemplated combination of glycerol and *Phyllanthus emblica* extract confers an increase in muscle volume and lean body mass. As readily understood by the skilled person, an increase in muscle volume and/or an increase in lean body mass are acute or transient effects on a subject as a result of administration of the contemplated composition(s). As the composition(s) of at least glycerol and *Phyllanthus emblica* extract are metabolized by the subject without additional administration, the effects may dissipate. Furthermore, the synergistic effects as disclosed herein are with respect to the subject having not ingested any of the contemplated composition for a period time (e.g., at least 24 hours).

With respect to measuring the muscle and lean body mass effects, these effects may be measured using any suitable technique. For example, muscle surrounding the femur (thigh) is measured by determining the girth (circumference) of the thigh (e.g., at mid-femur). Additionally, lean body mass may be measured using whole-body and/or segmental lower extremity dual-energy X-ray absorptiometry (DEXA or DXA) for measuring changes in lean mass as a result of fluid shifts and redistribution of volume from exercise-induced hyperemia. See, e.g., Sims et al., 2019, *PLoS ONE*, 14:e0213806, 1-16 and Kutac et al., 2019, *PLoS ONE*, 14:e0215599, 1-15, the entire contents of both of which are incorporated herein by reference.

Furthermore, the synergistic combination of glycerol and *Phyllanthus emblica* extract also confers an increase in physical performance. It is understood in the art that an increase in lean body mass correlates to an increase in physical performance relative to a given subject. See, e.g., Cawthon, 2015, *J. Clin. Densitom.*, 18:467-471, the entire content of which is incorporated herein by reference. In some embodiments, physical performance includes any physical exercise or daily activity, as well as work activities or procedures by one who is trained or skilled in physical activity.

The contemplated subject matter also includes methods for increasing muscle volume or increasing lean body mass in a muscle or muscle region within a subject. The contemplated method includes administering glycerol to the subject, administering *Phyllanthus emblica* extract to the subject, and exercising the muscle or the muscle region of the subject after administration of the glycerol and *Phyllanthus emblica* extract.

As disclosed herein, methods for increasing muscle volume or increasing lean body mass in a muscle or muscle region in a subject include administering glycerol to the subject in a daily dosage at between 0.10 to 25 grams and administering the *Phyllanthus emblica* extract to the subject in a daily dosage at between about 0.03 to 1.0 gram. Preferably, the method includes administering the *Phyllanthus emblica* extract and the glycerol in a weight ratio of between about 1:1 to 1:25, including all ratios therebetween and disclosed herein.

In typical embodiments, the disclosed inventive method for increasing muscle volume or increasing lean body mass includes administering the glycerol and the *Phyllanthus emblica* extract either concurrently or sequentially in either order.

Preferably, to allow for the glycerol and the *Phyllanthus emblica* extract to be absorbed in the subject, the method for increasing muscle volume or increasing lean body mass as disclosed herein also includes a period of at least 10 minutes between administering the synergistic composition (made of at least glycerol and the *Phyllanthus emblica* extract) and beginning the exercise session. This period of at least 10 minutes, may be 15, 20, or 30 minutes. Typically, the period of time between administering the synergistic composition and beginning the exercise session is about 30 minutes. Furthermore, the muscle, the whole-body lean body mass, or segmental lean body mass may be measured at any time prior to the administering of the glycerol and the *Phyllanthus emblica* extract to obtain a baseline measurement. Preferably, the measuring of the muscle, the whole-body lean body mass, and/or the segmental lean body mass occurs within 1 to 2 days of the administration of the glycerol and the *Phyllanthus emblica* extract to the subject. More preferably, the measuring of the muscle, the whole-body lean body mass, and/or a segmental lean body mass occurs no more than 24 hours prior to the administration of the glycerol and the *Phyllanthus emblica* extract to the subject.

In additional aspects, the contemplated method of increasing or improving physical performance (e.g., exercise), increasing muscle volume, or increasing the lean body mass of a subject includes administering to a subject an effective amount of the contemplated compositions having at least a synergistic combination of glycerol and *Phyllanthus emblica* extract to the subject. In some embodiments, the subject is a human. In some embodiments, the administration is oral administration. In some embodiments, the subject is administered about 0.1 mg to 50,000 mg of the composition per day. In some embodiments, the subject is administered about 1.0 mg to 20,000 mg of the composition per day. In some embodiments, the subject is administered about 1.0 mg to 10,000 mg of the composition per day. In some embodiments, the subject is administered about 10 mg to 10,000 mg of the composition per day. In some embodiments, the subject is administered about 50 mg to 3,000 mg of the composition per day. In some embodiments, the subject is administered about 50 mg to 1,000 mg of the composition per day. In some embodiments, the subject is in need of improved physical performance.

While the combination of glycerol and *Phyllanthus emblica* extract confer an unexpected synergy, the contemplated composition may also confer additional health benefits from additional components such as an additive and/or an excipient. These additional components may include medium chain triglycerides. In certain embodiments, the contemplated composition also includes one or more short chain triglycerides (e.g., short chain triglycerides selected from the group consisting of triacetin, tripropionin, and tributyrin). In some aspects, the contemplated composition also includes a short chain fatty acid. In additional aspects, the contemplated composition may include a botanical flavonoid and/or a botanical phenylpropanoid. In exemplary embodiments, the contemplated composition having a synergistic combination of glycerol and *Phyllanthus emblica* extract includes one or more additives selected from piceatannol, epicatechin, flavan-3-ols, resveratrol, pterostilbene, quercetin, theaflavin, kaempferol, hesperidin, caffeine, theacrine, methylliberine, urolithins, ellagic acid, ellagitannins, proanthocyanidins, dextrose, sucrose, maltodextrin, ribose, amylose, isomaltulose, amylopectin, rice oligodextrin, cluster dextrins, an amino acid, an amino acid salt, an amino acid ester, and/or an amino acid chelate.

More specifically, with respect to the amino acids or a salt, ester or chelate thereof, non-limiting examples include l-citrulline, l-leucine, l-isoleucine, l-valine, l-arginine, l-ornithine, glutamine, creatine, agmatine, taurine, and/or betaine. In other embodiments, the compositions further comprise or consist of one or more nitrate salts, including, but not limited to: potassium nitrate, sodium nitrate, and/or calcium nitrate.

In other embodiments, the glycerol and *Phyllanthus emblica* extract compositions may include vasoactives from di/tripeptides to penta-, nona- and decapeptides of plant, dairy, marine and animal origin. For example, the glycerol and *Phyllanthus emblica* extract compositions may include one or more of a protein concentrate or protein isolate selected from a whey protein concentrate, whey protein isolate, egg protein, beef protein, potato protein, calcium caseinate, rice protein concentrate, rice protein isolate, pea protein, and or hemp protein.

In some preferred embodiments, the additive may be coated with the glycerol and *Phyllanthus emblica* extract composition. For example, the glycerol and *Phyllanthus emblica* extract composition may be in a powder or particle form that is coated onto the additive. More specifically, a composition of *Phyllanthus emblica* extract and glycerol is in a weight ratio of 1:1 to 1:25 is in powder form that is coated on an additive or combination of additives as disclosed herein. In an exemplary embodiment, a powder made of 100 grams of *Phyllanthus emblica* extract and 1000 grams of glycerol is coated onto a supplement composition of an amino acid or an amino acid salt, ester or chelate thereof. For example, the amino acid supplement composition may include 1000 mg to 5,000 mg of 1-citrulline, 1-leucine, 1-isoleucine, 1-valine, 1-arginine, 1-ornithine, glutamine, creatine, agmatine, taurine, and/or betaine.

Additionally, or alternatively, the contemplated compositions of glycerol and *Phyllanthus emblica* extract may include excipients to aide in the manufacturing, appearance, and/or taste of the composition including colorings, flavorings and diluting agents; emulsifying, dispersing, and suspending agents; pharmaceutical solvents; antioxidants; and preservative agents.

The compositions and formulations according to the present invention can further compromise one or more acceptable carriers or excipients. Acceptable carriers and excipients may be combined with (e.g., mixed with or coated with) the composition of glycerol and *Phyllanthus emblica* extract with or without one or more additives. Carriers/excipients include fillers or extenders, binders, wetting agents, emulsifiers, and anti-caking agents.

Additionally or alternatively, the carrier may be any of the one or more additives disclosed herein, wherein the contemplated combination of glycerol and *Phyllanthus emblica* extract is coated in powder form onto any of the disclosed additives. As such, the additive may be used as the "platform" for the glycerol and *Phyllanthus emblica* extract. In addition to the additives disclosed herein, additional carriers also include a polysaccharide complex. Examples of a polysaccharide complex include highly branched galactose. Galactose may be highly branched with rhamnose, arabinose, and/or glucuronic acid. Preferably, a naturally occurring arabinogalactans (AG) is derived from plants and coated with the contemplated combination of glycerol and *Phyllanthus emblica* extract. For example, acacia fiber (e.g., 3,000 mg to 10,000 mg) may be coated with a powder of *Phyllanthus emblica* extract and glycerol in a weight ratio of from 1:1 to 1:25.

A wide number of acceptable carriers are well known in the art. The carrier need only be suitable for administration to a human and be able to act as a carrier without substantially affecting the desired activity of the composition. Also, the carrier(s) may be selected based on the desired administration route and dosage of the composition or formulation. For example, the compositions according to the present invention are suitable for are suitable for use on a variety of dosage forms such as liquid form and solid form (e.g., a chewable bar or wafer). In desirable embodiments as discussed below, the composition or formulation comprises a solid dosage form such as a tablet, caplet or capsule, lozenges, and chewing gum. Examples of suitable carriers for use in tablet, caplet and capsule compositions or formulations include, but are not limited to, inert organic and inert inorganic carrier materials such as gelatin, starch, magnesium stearate, talc, gums, silicon dioxide, stearic acid, cellulose and the like. Desirably, the carrier is substantially inert. In certain embodiments the composition or formulation is tablet, caplet, capsule or lozenge which uses pharmaceutically acceptable controlled release, time release or extended release technology; suitable technologies are known in the art.

Advantageously, one or more of the exemplary compositions described herein may be used as a composition, either alone or part of a more complex composition containing any number of additional ingredients. It will be readily apparent to those skilled in the art which specific ingredients may be beneficially included in such compositions. Furthermore, any one or more of the exemplary compositions disclosed herein may be administered in any dosage form common in the art. For example, the compositions disclosed herein may be administered in the form of a powder to be mixed in a liquid, or a solid dosage form such as a tablet, caplet, capsule, a ready-to-mix (e.g., ready-to-drink (RTD)) formulation, lozenges, nutritional bars, food bars or candy bars. More specifically, the contemplated composition may be an effective dosage of at least glycerol and *Phyllanthus emblica* extract formulated as a powder to be mixed in a liquid or in a solid dosage form to be formed as one or more tablets, one or more caplets, one or more capsules, one or more lozenges, one or more nutritional bars, one or more food bars, or one or more candy bars.

In some embodiments, the contemplated compositions disclosed herein further include one or more pharmaceutically acceptable excipients or carriers. In some embodiments, the composition is in the form of a powdered dietary supplement (e.g., ready-to-mix or RTD powder), capsule, tablet, caplet, or lozenge. In some embodiments, the compositions are formulated (e.g., agglomerated) to be shelf stable for six, twelve, eighteen, twenty, twenty-four, thirty, thirty-six, forty, forty-two, forty-eight months or longer.

In some embodiments, the contemplated composition is a nutraceutical. In some embodiments, the composition is a dietary ingredient and/or a dietary supplement. The composition may be a medical food or drug. Preferably, the composition is designated generally recognized as safe (GRAS) or as a new dietary ingredient (NDI).

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

As used herein, the term "nutraceutical" and "nutraceutically acceptable" are used to refer to any substance that is food or part of a food and provides medical and/or health benefits, including prevention and/or treatment of disease. Hence, compositions falling under the label of "nutraceutical" or "nutraceutically acceptable" may range from isolated nutrients, nutritional or dietary ingredients or dietary supplements and specific diets to genetically engineered designer foods, herbal products and processed foods such as beverages. In a more technical sense, the term has been used to refer to a product isolated or purified from foods, and generally sold in medicinal forms not associated with foods and demonstrated to have a physiological benefit or protection from chronic disease.

EXAMPLES

Exemplary studies were performed to study the effects of the combination of glycerol (e.g., Hydromax®, Glanbia Nutritionals) and *Phyllanthus emblica* extract (e.g., Capros®, Natreon, Inc.) in a clinical research study in resistance trained male subjects (N=5, having a median age of 28 years). The clinical research study was of a randomized, repeated measures design where the subjects served as their own control. This entire clinical research study took place at the Center for Applied Health Sciences, LLC. (CAHS, 4302 Allen Road, Suite 120, Stow, Ohio 44224). During this study, the subjects reported to CAHS in the morning after an overnight fast of 10 to 12 hours on four separate occasions to undergo one of the four distinct, treatment conditions as set forth below in Table 1. Each treatment was given on an empty stomach after a fast of 10 to 12 hours duration. Each treatment visit was one day in duration and each subject underwent a three-day washout between treatment visits with a 24-hour diet duplication.

Conversions to oral dosing of the Treatment 4 cohort expressed as mg/kg/dose and mg/m2 of body surface area/dose are noted in Table 2 for net glycerol dosing (the amount of glycerol from Hydromax® as indicated) and Table 3 for *Phyllanthus emblica* extract (Capros®) dosing.

TABLE 1

| Experimental Treatments 1-4 | |
|---|---|
| TREATMENT FORMULATION | TREATMENT CONDITIONS |
| TREATMENT 1 | 10 ounces of water 30 minutes before resistance training protocol initiated. Lower body resistance training protocol. |
| TREATMENT 2 | Hydromax ® 1500 mg (delivering 975 mg of glycerol) 30 minutes before resistance training protocol initiated. Lower body resistance training protocol. |
| TREATMENT 3 | *Phyllanthus emblica* extract (Capros ®) 150 mg 30 minutes before resistance training protocol initiated. Lower body resistance training protocol. |
| TREATMENT 4 | Hydromax ® 1350 mg (delivering 878 mg of glycerol) + *Phyllanthus emblica* extract 150 mg 30 minutes before resistance training protocol initiated. Lower body resistance training protocol. |

TABLE 2

Subjects 1-5 and Dosages of Net Glycerol

|  | TOTAL BODY MASS KILOGRAMS | HEIGHT IN CENTIMETERS | BODY SURFACE AREA IN M2 | MG/KG DOSE OF GLYCEROL | MG/M2 DOSE OF GLYCEROL |
|---|---|---|---|---|---|
| SUBJECT 1 | 77.7 | 176.5 | 1.944 | 11.30 | 1708.17 |
| SUBJECT 2 | 78.4 | 179.1 | 1.972 | 11.20 | 1731.76 |
| SUBJECT 3 | 94.9 | 190.5 | 2.237 | 9.25 | 1964.20 |
| SUBJECT 4 | 87.6 | 183.5 | 2.104 | 10.02 | 1848.42 |
| SUBJECT 5 | 88.1 | 181.6 | 2.093 | 9.96 | 1840.67 |

\* - Body Surface Area (BSA) computed using Mosteller formula of BSA = 0.016667 × $W^{0.5}$ × $H^{0.5}$ (Mosteller R D. "Simplified Calculation of Body-Surface Area". N Engl J Med 1987; 317: 1098)

TABLE 3

Subjects 1-5 and Dosages of *Phyllanthus emblica* extract (Capros ®)

|  | TOTAL BODY MASS KILOGRAMS | HEIGHT IN CENTIMETERS | BODY SURFACE AREA IN M2 | MG/KG DOSE OF CAPROS ® | MG/M2 DOSE OF CAPROS ® |
|---|---|---|---|---|---|
| SUBJECT 1 | 77.7 | 176.5 | 1.944 | 1.93 | 291.83 |
| SUBJECT 2 | 78.4 | 179.1 | 1.972 | 1.91 | 295.85 |
| SUBJECT 3 | 94.9 | 190.5 | 2.237 | 1.58 | 335.57 |
| SUBJECT 4 | 87.6 | 183.5 | 2.104 | 1.71 | 315.78 |
| SUBJECT 5 | 88.1 | 181.6 | 2.093 | 1.70 | 314.46 |

\* - Body Surface Area (BSA) computed using Mosteller formula of BSA = 0.016667 × $W^{0.5}$ × $H^{0.5}$ (Mosteller R D, supra).

After ingestion of assigned treatment materials and a 30-minute waiting period, each subject performed a lower body resistance training protocol which consisted of seated leg/knee extensions and loaded goblet squats for three sets of 10 to 12 repetitions per set with a 60 second inter-set rest period. Subjects waited 120 seconds between exercises. Training sessions were duplicated for each subject at each treatment for total work output (repetitions, sets, & weight load).

Measurements (i.e., clinical endpoints) obtained for each subject immediately after the conclusion of each treatment and lower body resistance training protocol included: 1) Thigh girth/circumference measured at mid-femoral landmark; and 2) Whole-Body and Segmental Lower Extremity Dual-energy X-ray absorptiometry (DEXA) for measuring changes in lean mass measures as a result of fluid shifts and redistribution of volume from exercise-induced hyperemia. The results for each of Treatments 1 to 4 were averaged over the Subjects 1-5 and the average increase in girth of thigh, increase in leg lean mass, and total body lean mass are shown in Table 4 and discussed below.

TABLE 4

Treatment Results: Increase in Muscle Volume and Lean Mass

|  | AVERAGE INCREASE IN GIRTH/CIRCUMFERENCE OF THIGH (CENTIMETERS) | AVERAGE INCREASE IN LEG LEAN MASS (GRAMS) | AVERAGE INCREASE IN TOTAL BODY LEAN MASS (GRAMS) |
|---|---|---|---|
| TREATMENT 1 | 1.12 | 304.3 | 30.4 |
| TREATMENT 2 | 1.32 | 328.1 | 98.3 |
| TREATMENT 3 | 1.66 | 355.4 | 149.3 |
| TREATMENT 4 | 2.21 | 562.2 | 693.1 |

Study subjects after undergoing Treatment 1 were measured to have an average increase of 1.12 centimeters in thigh (mid-femoral) circumference, an average 304.3 gram increase in leg lean mass, and an average 30.4 gram increase in total body mass as measured immediately after the lower body resistance training protocol.

Study subjects after undergoing Treatment 2 were measured to have an average increase of 1.32 centimeters in thigh (mid-femoral) circumference, an average 328.1 gram increase in leg lean mass, and an average 98.3 gram increase in total body mass as measured immediately after the lower body resistance training protocol.

Study subjects after undergoing Treatment 3 were measured to have an average increase of 1.66 centimeters in thigh (mid-femoral) circumference, an average 355.4 gram increase in leg lean mass, and an average 149.3 gram increase in total body mass as measured immediately after the lower body resistance training protocol.

Study subjects after undergoing Treatment 4 were measured to have an average increase of 2.21 centimeters in thigh (mid-femoral) circumference, an average 562.2 gram increase in leg lean mass, and an average 693.1 gram increase in total body mass as measured immediately after the lower body resistance training protocol.

The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about", the invention includes an embodiment in which the exact value is recited. For any embodiment of the invention in which a numerical value is not prefaced by "about", the invention includes an embodiment in which the value is prefaced by "about".

As used herein, the term "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought-to-be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of increasing muscle volume or increasing lean body mass in a muscle or muscle region in a subject, comprising:
   administering via ingestion a composition that comprises a synergistic combination of (i) glycerol at between about 0.10 to about 25 grams, and (ii) a *Phyllanthus emblica* extract at between about 0.03 to about 1.0 gram;
   wherein the synergistic combination of *Phyllanthus emblica* extract to glycerol has a weight ratio of between about 1:1 to about 1:25;
   exercising the muscle or the muscle region of the subject; and
   wherein ingestion of the composition is in an amount that increases the muscle volume or that increases the lean body mass in the muscle or the muscle region in the subject upon exercise.

2. The method of claim 1, wherein the synergistic combination of *Phyllanthus emblica* extract to glycerol has a weight ratio of between about 1:1 to about 1:10.

3. The method of claim 1, wherein the composition comprises glycerol at between about 9.25 to about 11.30 mg per kilogram (mg/kg) weight of the subject and the composition comprises *Phyllanthus emblica* extract at between about 1.58 to about 1.93 mg/kg weight of the subject.

4. The method of claim 1, wherein the composition is formulated as a powder to be mixed in a liquid.

5. The method of claim 1, wherein the composition is formulated as one or more tablets, one or more caplets, one or more capsules, one or more lozenges, one or more nutritional bars, one or more food bars, or one or more candy bars.

6. The method of claim 1, wherein the composition is formulated as a liquid.

7. The method of claim 6, wherein the composition is formulated as a ready-to-drink formulation.

8. The method of claim 1, wherein the synergistic combination of *Phyllanthus emblica* extract and glycerol make up at least 5% of the total weight of the administered composition.

9. The method of claim 1, wherein the composition further comprises an amino acid.

10. The method of claim 1, further comprising a period of at least 10 minutes between the administering and the exercising wherein the muscle or the muscle region is not exercised.

11. The method of claim 1, wherein the muscle or the muscle region is measured prior to the administering of the composition and the method further comprises measuring the muscle or the muscle region after the exercising.

12. The method of claim 11, wherein the increase in muscle volume comprises measuring the girth of the muscle or the muscle region and the increase in lean body mass comprises measuring using the muscle or whole body using Dual-energy X-ray absorptiometry (DEXA).

* * * * *